United States Patent [19]

Giede et al.

[11] Patent Number: 5,612,024
[45] Date of Patent: Mar. 18, 1997

[54] COSMETIC PREPARATIONS FOR THE HAIR

[75] Inventors: Karl Giede, Hilden; Kurt Seidel, Duesseldorf; Reinhard Mueller, Erkelenz; Detlef Hollenberg, Erkrath, all of Germany

[73] Assignee: Henkel Kommanditgesellschaft auf Aktien, Duesseldorf, Germany

[21] Appl. No.: 414,149

[22] Filed: Mar. 30, 1995

Related U.S. Application Data

[63] Continuation of Ser. No. 122,517, Sep. 27, 1993, abandoned.

[30] Foreign Application Priority Data

Mar. 27, 1991 [DE] Germany .......................... 41 09 999.0

[51] Int. Cl.$^6$ ...................................................... A61K 7/06
[52] U.S. Cl. .................... 424/70.11; 424/70.14; 424/401; 424/DIG. 2
[58] Field of Search ............................ 424/401, DIG. 2, 424/70.11, 70.14; 252/DIG. 13

[56] References Cited

U.S. PATENT DOCUMENTS

| | | | |
|---|---|---|---|
| 4,075,131 | 2/1978 | Sterling | 252/542 |
| 4,269,824 | 5/1981 | Villamarin et al. | 424/70 |
| 4,364,837 | 12/1982 | Pader | 424/70 |
| 4,393,886 | 7/1983 | Strasilla et al. | 132/202 |
| 4,402,936 | 9/1983 | Okumura et al. | 424/70.15 |
| 4,668,508 | 5/1987 | Grollier et al. | 424/70.13 |
| 4,690,818 | 9/1987 | Puchalski, Jr. et al. | 424/70.14 |
| 4,814,101 | 3/1989 | Schieferstein et al. | 252/174.23 |
| 4,847,076 | 7/1989 | Deshpande et al. | 424/70.13 |
| 4,900,545 | 2/1990 | Wisotzki et al. | 424/70 |
| 4,906,460 | 3/1990 | Kim et al. | 424/70 |
| 4,994,088 | 2/1991 | Ando et al. | 8/426 |

FOREIGN PATENT DOCUMENTS

| | | |
|---|---|---|
| 0052489 | 5/1982 | European Pat. Off. . |
| 0395332 | 10/1990 | European Pat. Off. . |
| 2655544 | 6/1991 | France . |
| 2817369 | 10/1978 | Germany . |
| 3528168 | 11/1985 | Germany . |
| 3708451 | 10/1988 | Germany . |
| 3929973 | 3/1991 | Germany . |
| 7773485 | 6/1977 | Japan . |
| 62-178510 | 8/1987 | Japan . |
| 63-054313 | 3/1988 | Japan . |
| 2104091 | 3/1983 | United Kingdom . |
| 2113245 | 8/1983 | United Kingdom . |
| 2148714 | 6/1985 | United Kingdom . |
| 2188948 | 10/1987 | United Kingdom . |
| 8703196 | 6/1987 | WIPO . |

OTHER PUBLICATIONS

Seifen Ole Fette Wasche, vol. 113, No. 17, Oct. 1987, Augsburg, DE, pp. 617–622 "Quaternised Proteins In Modern Hair Care", Chester et al. (Article Not Available).
Ärztl. Kosmetologie, 20, 498–502, 1990.

*Primary Examiner*—John C. Bleutge
*Assistant Examiner*—Robert H. Harrison
*Attorney, Agent, or Firm*—Ernest G. Szoke; Wayne C. Jaeschke; Real J. Grandmaison

[57] ABSTRACT

The invention concerns the use of combinations of active substances, consisting of (a) a cationic derivative of a protein hydrolyzate and (b) a carbohydrate and/or (c) a cationic, anionic or ampholytic polymer, in hair-cleaning and hair-care agents, thus improving the qualities of the hair, in particular its brittleness and its ease of combing when dry.

16 Claims, No Drawings

COSMETIC PREPARATIONS FOR THE HAIR

This application is a continuation of application Ser. No. 08/122,517 filed on Sep. 27, 1993, now abandoned.

FIELD OF THE INVENTION

This invention relates to cosmetic preparations for the hair containing a special combination of active substances.

STATEMENT OF RELATED ART

Nowadays, human hair is treated in many different ways with hair-cosmetic preparations, including for example the washing of hair with shampoos and shower preparations and the bleaching, dyeing and shaping of hair with wave preparations, tinting preparations and styling preparations. Almost every form of hair treatment can result in unwanted damage to the hair structure. Such damage is reflected inter alia in poor wet and dry combability, in increased electrostatic charging, in reduced maximum tensile strength and breaking elongation of the hair and in the poor appearance of hair styles.

One known method of overcoming these drawbacks is to subject the hair to aftertreatment with suitable active substances, generally cationic surfactants, which may optionally be combined with other substances.

However, this approach is unsatisfactory in many respects.

Thus, it is known that cationic surfactants are only suitable for the treatment of non-greasy hair. By contrast, their use on greasy hair is problematical because they impose an additional burden on the hair and intensify the natural refatting process.

In addition, the quaternary ammonium compounds typically used as cationic surfactants show inadequate biodegradability so that their use should be avoided or reduced on ecological grounds.

Another unsatisfactory aspect is that any treatment with cationic surfactants generally has to be carried out in a separate step, normally by rinsing, because cationic surfactants often cannot be incorporated in preparations containing anionic surfactants, such as shampoos for example.

Another group of substances used to prevent unwanted damage to hair are the protein hydrolyzates.

DE 35 28 168 describes synergistic mixtures of protein hydrolyzates and mono- , di- and oligo-saccharides which are distinguished by good film-forming properties as required for the treatment of unwanted damage to hair. Unfortunately, mixtures of known protein hydrolyzates and saccharities have the disadvantage that the so-called Maillard reaction can take place during storage at room temperature. This results in degradation of the active substance and turns the preparations brown in color. This brown coloration is generally not accepted by the consumer so that it has to be masked by addition of increased quantities of dyes.

DESCRIPTION OF THE INVENTION

Object of the Invention

Accordingly, there is still a need for hair cosmetic preparations which are distinguished by a reduction in unwanted damage to the hair.

SUMMARY OF THE INVENTION

It has now surprisingly been found that hair cosmetic preparations containing a cationically derivatized protein hydrolyzate (A) and a carbohydrate (B) and/or a cationic, anionic or ampholytic polymer (C) have a far less unfavorable influence on the hair. The use of these combinations of active substances increases the tensile strength of hair and also provides for better style retention and improved volume. In addition, no Maillard reaction occurs in the combinations (A)+(B) and (A)+(B)+(C).

Accordingly, the present invention relates to preparations containing typical constituents for the washing and care of hair, characterized in that they contain a combination of active substances consisting of (A) a cationically derivatized protein hydrolyzate and (B) a carbohydrate and/or (C) a cationic, anionic or ampholytic polymer.

Cationically derivatized protein hydrolyzates (A) are mixtures of substances which may be obtained, for example, by reaction of alkali-, acid- or enzyme-hydrolyzed proteins with glycidyl trialkyl ammonium salts or 3-halo-2-hydroxypropyl trialkyl ammonium salts.

Proteins used as starting materials for the protein hydrolyzates may be of both animal and vegetable origin. Typical starting materials are, for example, keratin, collagen, elastin, soya protein, milk protein, wheat protein, silk protein and almond protein.

Mixtures having molecular weights in the range from about 100 to about 50,000 Daltons are formed by the hydrolysis. Typical average molecular weights are in the range from about 500 to about 1000 Dalton.

Further particulars of cationic derivatization can be found inter alia in Japanese patent application 77/73485 (Chemical Abstracts, Abstract 90:174508v).

DESCRIPTION OF PREFERRED EMBODIMENTS

The cationically derivatized protein hydrolyzates advantageously contain one or two long alkyl chains containing 8 to 22 carbon atoms and, accordingly, two or one short alkyl chain containing 1 to 4 carbon atoms. Compounds containing one long alkyl chain are preferred.

Preferred compounds (A) correspond to formula (I):

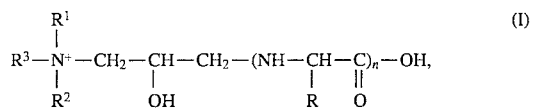

in which R represents the side chains of the amino acids of the protein, $R^1$ and $R^2$ independently of one another represent alkyl chains containing 1 to 4 carbon atoms and $R^3$ represents an alkyl chain containing 8 to 22 carbon atoms.

A commercially available product is Lamequat®L (Chemische Fabrik Grtinau). It has the following structure:

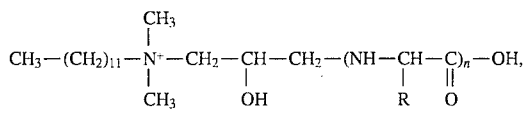

in which R represents the side chains of the amino acids of collagen. Its CTFA name is Lauryldimonium Hydroxypropylamino Hydrolyzed Animal Protein. This product is a particularly preferred component (A).

According to the invention, both monosacchafides and oligosacchafides, such as for example cane sugar, lactose and raffinose, may be used as the carbohydrates (B). The use of monosaccharides is preferred. Preferred monosachafides are compounds containing 5 or 6 carbon atoms.

Suitable pentoses and hexoses are, for example, ribose, arabinose, xylose, lyxose, allose, altrose, glucose, mannose, gulose, idose, galactose, talose and fructose. Arabinose, glucose, galactose and fructose are preferred carbohydrates, glucose being particularly preferred.

In addition, derivatives of these pentoses and hexoses, such as the corresponding onic and uronic acids (sugar acids), sugar alcohols and glycosides, may also be used in accordance with the invention. Preferred sugar acids are gluconic acid, glucuronic acid, sugar acid, mannosugar acid and mucic acid. Preferred sugar alcohols are sorbitol, mannitol and dulcitol. Preferred glycosides are the methyl glucosides.

Quaternized carbohydrates may also be used as component (B) in accordance with the invention. The commercial product Glucquat®100 (CTFA name: Lauryl Methyl Gluceth-10 Hydroxypropyl Dimonium Chloride) is a preferred quaternized carbohydrate.

Since the carbohydrates used are normally obtained from natural raw materials, such as starch, the carbohydrates generally have the configurations corresponding to these raw materials (for example D-glucose, D-fructose and D-galactose).

The following are examples or cationic polymers (C) suitable for use in accordance with the invention:

Suitable cationic polymers (C) are, for example:

Quaternized cellulose derivatives of the type commercially available under the names of Celquat® and Polymer JR®. The compounds Celquat H 100, Celquat L 200 and Polymer JR® 400 are preferred quaternized cellulose derivatives.

Copolymers of vinyl pyrrolidone with quaternized derivatives of dialkyl aminoacrylate and methacrylate, for example vinyl pyrrolidone/dimethyl aminomethacrylate copolymers quaternized with diethyl sulfate. Compounds such as these are commercially available under the names of Gafquat® 734 and Gafquat® 755.

Vinyl pyrrolidone/methoimidazolinium chloride copolymers of the type commercially available under the name of Luviquat®.

Polymeric dimethyl diallyl ammonium salts and copolymers thereof with esters and amides of acrylic acid and methacrylic acid. The products commercially available under the names of Merquat® 100 {poly(dimethyl diallyl ammonium chloride)} and Merquat® 550 (dimethyl diallyl ammonium chloride/acrylamide copolymer) are examples of such cationic polymers.

Examples of anionic polymers suitable for the purposes of the invention are:

Polyacrylic and polymethacrylic acids, salts thereof, copolymers thereof with esters and amides of (meth)acrylic acid and derivatives thereof obtained by crosslinking with polyfunctional agents. Compounds of this type are commercially available, for example, under the names of Carbopol® 934, Carbopol®934P, Carbopol® 940, Carbopol® 950, Carbopol® 980 and Hostacerin® PN 73.

Polyoxycarboxylic acids, such as polyketocarboxylic and polyaldehydocarboxylic acids and salts thereof, such as for example POC® HS 5060 and POC® AS 5060.

Polymers and copolymers of crotonic acid with esters and amides of (meth)acrylic acid, such as vinyl acetate/ crotonic acid and vinyl acetate/vinyl propionate/crotonic acid copolymers. Compounds of this type are commercially available as Luviset® CA-66 and Luviset® CAP.

In the context of the invention, ampholytic polymers are understood to be amphoteric polymers, i.e. polymers which contain both free amino groups and free —COOH or $SO_3H$ groups in the molecule and which are capable of forming inner salts, zwitterionic polymers containing quaternary ammonium groups and —COO$^-$ or —SO$_3^-$ groups in the molecule and polymers containing —COOH or $SO_3H$ groups and quaternary ammonium groups.

One example of an ampholytic polymer suitable for use in accordance with the invention is the acrylic resin commercially available as Amphomer® which is a copolymer of tert-butyl aminoethyl methacrylate, N-(1,1,3,3-tetramethylbutyl)-acrylamide and two or more monomers from the group consisting of acrylic acid, methacrylic acid and simple esters thereof.

Other ampholytic polymers suitable for use in accordance with the invention are the compounds mentioned in GB-A-2,104,091, EP-A47 714, EP-A-217 274, EP-A-283 817 and DE-A-28 17 369.

Preferred ampholytic polymers are polymers consisting essentially of (a) monomers containing quaternary ammonium groups corresponding to general formula (II):

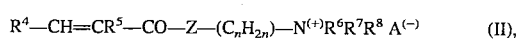

$$R^4\!-\!CH\!=\!CR^5\!-\!CO\!-\!Z\!-\!(C_nH_{2n})\!-\!N^{(+)}R^6R^7R^8\ A^{(-)} \qquad (II),$$

in which $R^4$ and $R^5$ independently of one another represent hydrogen or a methyl group and $R^6$, $R^7$ and $R^8$ independently of one another represent $C_{1-4}$ alkyl groups, Z is an NH group or an oxygen atom, n is an integer of 2 to 5 and $A^{(-)}$ is the anion of an organic or inorganic acid; and (b) monomeric carboxylic acids corresponding to general formula (III):

$$R^9\!-\!CH\!=\!CR^{10}\!-\!COOH \qquad (III)$$

in which $R^9$ and $R^{10}$ independently of one another represent hydrogen or methyl groups.

These compounds may be used in accordance with the invention both directly and in salt form, i.e. after neutralization of the polymers, for example with an alkali metal hydroxide. Full particulars of the production of these polymers can be found in DE-A-39 29 973. Polymers in which monomers of type (a), where $R^6$, $R^7$ and $R^8$ are methyl groups, Z is an NH group and $A^{(-)}$ is a halide, methoxysulfate or ethoxysulfate ion, are most particularly preferred. Acrylamidopropyl trimethyl ammonium chloride is a particularly preferred monomer (a). Acrylic acid is preferably used as monomer (b) for the polymers mentioned.

The active substances (A) are present in a quantity of 0.1 to 10% by weight, based on the preparation as a whole. Concentrations of 0.5 to 5% by weight are preferred.

The active substances (B) are also present in a quantity of 0.1 to 10% by weight, based on the preparation as a whole. Concentrations of 0.5 to 5% by weight are preferred.

It has been found that a particularly advantageous effect is obtained when compounds (A) and (B) are present in a ratio by weight of 0.5:1 to 2:1. Preparations in which components (A) and (B) are present in substantially equal parts by weight are particularly preferred.

The active substances (C) are preferably present in the preparations according to the invention in a quantity of 0.1 to 5% by weight and, more preferably, in a quantity of 0.2 to 2% by weight, based on the preparation as a whole.

Although the combinations of active substance (A) and active substance (B) or active substance (A) and active substance (C) have a surprisingly strong effect on the structure and properties of the hair, it has been found that a further unexpectedly marked increase in effect occurs where all three active substances are combined.

In one preferred embodiment, therefore, the preparations according to the invention contain both active substance (B) and active substance (C) in addition to active substance (A). Combinations of (A), (B) and (C), in which (C) is an ampholytic polymer, are most particularly preferred.

The preparations according to the invention may be used both in hair treatment processes in which the preparation is rinsed out from the hair after use and in hair treatment processes where the preparation remains in the hair.

Preparations which normally are rinsed from the hair after use are, for example, shampoos, wave preparations and coloring preparations. Products which normally remain in the hair are, for example, hair setting preparations, hair tonics and blow-wave preparations. In addition to the compulsory components, any other auxiliaries and additives typical of the application in question may be present, depending on the type and preparation.

In the case of shampoos, such auxiliaries and additives besides water as the base are anionic, nonionic and zwitterionic surfactants, pearlescers, perfumes, pH regulators, dyes, preservatives, optionally alkoxylated fatty acids and fatty alcohols and viscosity regulators.

Hair rinses, which are also water-based in most cases, generally contain quaternary ammonium compounds, lower alcohols, solubilizers, active principles, such as panthenol for example, nonionic polymers, viscosity regulators and perfume oils.

In addition to water, hair setting preparations generally contain lower alcohols, surfactants, preferably nonionic surfactants, stabilizers, cationic and/or anionic polymers, pH regulators and—in the case of setting foams—propellants.

Hair coloring preparations normally contain substantive dyes and/or oxidation dye precursors (modifiers, developer components), surfactants, fatty alcohols and pH regulators.

In addition to a reducing agent (thioglycolic acid, thiolactic acid), wave preparations generally contain pH regulators, surfactants, complexing agents, solubilizers, fatty alcohols and perfume oils. The corresponding fixing solutions contain oxidizing agents, such as hydrogen peroxide and potassium bromate, instead of the reducing agent.

EXAMPLES

1. Determination of hair properties
Four shampoos were tested, their compositions being set out in Table 1 below.
a) Elongation measurements on treated hair Alkinco type 6621 hair tresses (tress length: 12 cm) were used for the measurements.

The tresses were treated for 20 minutes with the test shampoo, then rinsed for about 30 seconds and dried with a blow dryer for about 1.5 hours at 38° C. The tresses were then ultrableached for 20 minutes (composition of the ultrableach: 6% by weight of hydrogen peroxide, 15% by weight of ammonium peroxydisulfate, conc. ammonia ad pH 9.4, remainder water) and rinsed with water for about 1 minute. The wet tresses were then shampooed, rinsed and dried as described above. The tresses were then cold-waved (wave solution: 7% by weight thioglycolic acid, conc. ammonia ad pH 9.0, remainder water), rinsed with water (38° C.) for about 1 minute and treated with a fixing solution (2% by weight hydrogen peroxide, citric acid ad pH 4.0, remainder water), shampooed, rinsed and dried as described above. The cycle of ultrableaching, rinsing, shampooing, rinsing, drying, cold waving, rinsing, fixing, rinsing, shampooing, rinsing and drying was then repeated another two times. For the dry measurement, the tresses were heated in air at 38° C. For the wet measurements, the tresses were stored in water until just before the measurement.

The following values were determined:
Maximum breaking stress (tensile force at which the hair breaks)
15% Elongation value (tensile force at which the hair is elongated by 15%)
Breaking elongation (% elongation at which the hair breaks)
Brittleness Particulars of the measuring process can be found in the literature (Ärztl. Kosmetologie 15, 347–355 (1985) and Parfümerie & Kosmetik 72, 74–81 (1991)).

Brittleness is determined as the percentage of hairs which show a break at 20% elongation and less.

TABLE 1

| Test shampoos | | | | |
|---|---|---|---|---|
| Component | 1 | 2 | 3 | 4 |
| Texapon ® N25[1] | 43 | 43 | 43 | 43 |
| Dehyton ® K-IS[2] | 10 | 10 | 10 | 10 |
| Euperlan ® PK 810 IS[3] | 5 | 5 | 5 | 5 |
| Akypo ® RLM 100 NV[4] | 5 | 5 | 5 | 5 |
| EDENOR ® KPK C12–18 + 9.2 EO[5] | 1 | 1 | 1 | 1 |
| Preservative | 0.3 | 0.3 | 0.3 | 0.3 |
| Sodium chloride | 1.2 | 0.25 | 0.19 | 0.19 |
| Perfume oil, dyes | 1.1 | 1.1 | 1.1 | 1.1 |
| Lamequat ® L[6] | — | 3 | 3 | 3 |
| D glucose | — | 3 | 3 | 3 |
| Polymer JR ® 400[7] | — | — | 0.2 | — |
| Polymer P1 acc. to DE 39 29 973[8] | — | — | — | 1 |
| Citric acid ad pH | 7.2 | 7.2 | 7.2 | 7.0 |
| Water | ← ad 100 → | | | |
| Viscosity [mPas] | 9300 | 9700 | 8500 | 9200 |

[1]Sodium lauryl ether sulfate; CTFA name: Sodium Laureth Sulfate (about 28% active substance in water) (HENKEL)
[2]Fatty acid amide derivative, betaine structure, corresponding to the formula $R-CONH-(CH_2)_3-N^+(CH_3)_2-CH_2-COO^-$; CFTA name: Cocoamidopropyl Betaine (about 30% active substance in water) (HENKEL)
[3]Mixture of fatty alcohol ether sulfates with pearlescing substances; CTFA name: Glycol Distearate (and) Sodium Laureth Sulfate (and) Cocoamide MEA (and) Laureth-9 (about 37% active substance, including about 13% anionic surfactant, in water) (HENKEL)
[4]$C_{12-14}$ fatty alcohol + 10 EO acetic acid sodium salt; CTFA name: Sodium Laureth-11 Carboxylate (22% active substance) (CHEM-Y)
[5]Coconut palm kernel oil fatty acid ($C_{12-18}$) + 9.2 ethylene oxide (HENKEL)
[6]Cationic protein hydrolyzate corresponding to the formula:

$$CH_3-(CH_2)_{11}-\underset{\underset{CH_3}{|}}{\overset{\overset{CH_3}{|}}{N^+}}-CH_2-\underset{\underset{OH}{|}}{CH}-CH_2-(NH-\underset{\underset{R}{|}}{CH}-\overset{\overset{O}{\|}}{C})_n-OH,$$

(R = side chains of the aminoacids of collagen); CTFA name: Lauryldimonium Hydroxypropylamino Hydrolyzed Animal Protein (about 35% dry matter) (CHEMISCHE FABRIK GRUNAU)
[7]Quaternized hydroxyethyl cellulose (Union Carbide)
[8]Polymer of acrylamidopropyl trimethyl ammonium chloride and acrylic acid in a molar ratio of 3:1, neutralized with NaOH (20% active substance in water).

| | Shampoo | | | |
|---|---|---|---|---|
| | 1 | 2 | 3 | 4 |
| Wet measurement | | | | |
| Maximum breaking stress [mN] | 380 | 462 | 390 | 511 |
| 15% Elongation value [mN] | 268 | 307 | 290 | 304 |
| Dry measurement | | | | |
| Maximum breaking stress [mN] | 477 | 446 | 461 | 501 |

-continued

| | Shampoo | | | |
|---|---|---|---|---|
| | 1 | 2 | 3 | 4 |
| 15% Elongation value [mN] | 432 | 401 | 403 | 418 |
| Breaking Elongation [%] | 21 | 28 | 28 | 42 |
| Brittleness [%] | 68 | 52 | 52 | 30 | b) Determination of the dry combing work

The dry combing work was determined on brown hair (Alkinco 6634, tress length 12 cm, tress weight 1 g) in the form of a comparison of paired mean values. To determine the zero value, the tresses were rinsed with water (1 l/min, 38° C.) for 1.5 minutes and combed out. The tresses were then dried with a blow dryer for 40 minutes at 45° C. After conditioning for 12 hours at 30° C./40% relative air humidity, the combing work was determined. The tresses were then treated with 100 g of the formulation for 5 minutes and then rinsed, dried and conditioned as described above. The dry combing work was then determined. Particulars of the measuring process can be found in the literature (Ärztl. Kosmetologie 20, 498–502 (1990)).

The following combing work values were measured:

| | Dry Combing Work, mJ | | |
|---|---|---|---|
| Shampoo | Before | After | b/a, % |
| 1 | 6.5 | 6.5 | 100 |
| 2 | 5.1 | 7.6 | 150 |
| 3 | 5.5 | 9.7 | 175 |
| 4 | 7.6 | 10.9 | 144 |

2. Application Examples

| | % by weight |
|---|---|
| a) Hair setting foam | |
| EUMULGIN ® | 0.5 |
| LUVISET ® | 4.5 |
| AMP ® | 0.4 |
| GAFQUAT ® | 0.5 |
| D glucose | 0.2 |
| Lamequat ® L | 0.2 |
| Ammonia (25% solution) | 0.1 |
| Perfume oil | 0.13 |
| Ethanol | 5.0 |
| Drivosol ® 3.5[13] | 7.0 |
| Water | ad 100 |
| b) Rinse | |
| Cremophor ® RH 40[14] | 1.5 |
| Dehyquart ® SP[15] | 1.0 |
| Luviskol ® K 30[16] | 1.0 |
| Panthenol | 1.0 |
| D glucose | 2.0 |
| Lamequat ® L | 1.0 |
| Polymer Pl acc. to DE 39 29 973 | 3.0 |
| Hydroxyethyl cellulose | 1.8 |
| Ethanol (96%) | 12.0 |
| Water | ad 100 |

[9]Oleyl alcohol + 5 ethylene oxide; CTFA name: Oleth-5 (HENKEL)
[10]Vinyl acetate/crotonic acid copolymer (90:10) (BASF)
[11]2-Amino-2-methyl propanol (95% active substance, remainder water) (ANGUS CHEMIE)
[12]Dimethylaminoethyl methacrylate/vinyl pyrrolidone copolymer quaternized with diethyl sulfate; CTFA name: Polyquaternium 11 (about 19% active substance in water) (GAF)
[13]Propane/isobutane/butane/dimethyl ether mixture (24:72:3:1) (HÜLS)
[14]Hydrogenated castor oil reacted with 45 moles of ethylene oxide per mole of castor oil (BASF)

| | % by weight |
|---|---|

[15]Oxyethyl alkylammonium phosphate; CTFA name: Quaternium-52 (50% active substance in water) (HENKEL)
[16]Polyvinyl pyrrolidone (95% active substance, remainder water) (BASF).

The invention claimed is:

1. Preparations for the cleaning and care of hair consisting of
   (A) 0.1 to 10% by weight of a compound corresponding to formula (I):

$$R^3-\underset{\underset{R^2}{|}}{\overset{\overset{R^1}{|}}{N^+}}-CH_2-\underset{\underset{OH}{|}}{CH}-CH_2-(NH-\underset{\underset{R}{|}}{CH}-\overset{\overset{}{\|}}{C})_n-OH, \quad (I)$$

in which R represents the side chains of the amino acids of the protein, $R^1$ and $R^2$ independently of one another represent alkyl chains containing 1 to 4 carbon atoms and $R^3$ represents an alkyl chain containing 8 to 22 carbon atoms, (B) 0.1 to 10% by weight of a carbohydrate selected from the group consisting of monosaccharides, oligosaccharides, onic and uronic acids, sugar alcohols and glycosides; and
   (C) 0.1 to 5% by weight of a cationic or ampholytic polymer, based on the weight of said preparations.

2. Preparations as claimed in claim 1 wherein (A) is a compound of formula (I) in which $R^1$ and $R^2$ are methyl groups and $R^3$ is a lauryl group.

3. Preparations as claimed in claim 2, wherein said carbohydrate contains 5 or 6 carbon atoms.

4. Preparations as claimed in claim 3, wherein said carbohydrate is glucose.

5. Preparations as claimed in claim 4, wherein (C) is an ampholytic polymer.

6. Preparations as claimed in claim 5, wherein component (A) is present in a quantity of 0.5 to 5% by weight, based on the preparation as a whole.

7. Preparations as claimed in claim 6, wherein component (B) is present in a quantity of 0.5 to 5% by weight, based on the preparation as a whole.

8. Preparations as claimed in claim 7, wherein component (C) is present in a quantity of 0.1 to 2% by weight, based on the preparation as a whole.

9. A hair treatment process wherein a preparation as claimed in claim 1 is applied to the hair and is rinsed out again after a contact time.

10. A hair treatment process wherein a preparation as claimed in claim 1 is applied to the hair and is left thereon.

11. Preparations as claimed in claim 1, wherein said carbohydrate is glucose.

12. Preparations as claimed in claim 1, wherein said carbohydrate contains 5 or 6 carbon atoms.

13. Preparations as claimed in claim 1, wherein (C) is an ampholytic polymer.

14. Preparations as claimed in claim 4, wherein component (A) is present in a quantity of 0.5 to 5% by weight, based on the preparation as a whole.

15. Preparations as claimed in claim 5, wherein component (B) is present in a quantity of 0.5 to 5% by weight, based on the preparation as a whole.

16. Preparations as claimed in claim 5, wherein component (C) is present in a quantity of 0.1 to 2% by weight, based on the preparation as a whole.

* * * * *